(12) United States Patent  
Bruszewski (10) Patent No.: US 8,100,960 B2
(45) Date of Patent: Jan. 24, 2012

(54) BLOUSED STENT-GRAFT AND FENESTRATION METHOD

(75) Inventor: Walter Bruszewski, Guerneville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 221 days.

(21) Appl. No.: 12/052,591

(22) Filed: Mar. 20, 2008

(65) Prior Publication Data

US 2009/0240316 A1 Sep. 24, 2009

(51) Int. Cl.
*A61F 2/06* (2006.01)

(52) U.S. Cl. ...................................................... 623/1.13

(58) Field of Classification Search .................. 623/1.15, 623/1.16, 1.13, 1.35, 1.3–1.31, 1.36, 1.14, 623/1.28, 1.29, 1.17
See application file for complete search history.

(56) References Cited

U.S. PATENT DOCUMENTS

| | | | |
|---|---|---|---|
| 5,720,776 A * | 2/1998 | Chuter et al. ................ | 623/1.36 |
| 5,957,949 A * | 9/1999 | Leonhardt et al. .......... | 623/1.24 |
| 6,352,554 B2 * | 3/2002 | De Paulis ..................... | 623/1.26 |
| 6,770,090 B2 * | 8/2004 | Gantt et al. ................. | 623/1.35 |
| 7,220,274 B1 * | 5/2007 | Quinn .......................... | 623/1.13 |
| 2003/0176912 A1 * | 9/2003 | Chuter et al. ................ | 623/1.13 |
| 2004/0098096 A1 * | 5/2004 | Eton ............................. | 623/1.13 |
| 2005/0119730 A1 * | 6/2005 | Howat et al. ................ | 623/1.29 |
| 2005/0131518 A1 * | 6/2005 | Hartley et al. ............... | 623/1.13 |
| 2005/0228488 A1 * | 10/2005 | Nazzaro ....................... | 623/1.26 |
| 2005/0273155 A1 * | 12/2005 | Bahler et al. ................ | 623/1.13 |
| 2006/0195172 A1 * | 8/2006 | Luo et al. ..................... | 623/1.13 |
| 2007/0198079 A1 * | 8/2007 | Casey et al. ................. | 623/1.13 |

* cited by examiner

*Primary Examiner* — S. Thomas Hughes
*Assistant Examiner* — Jocelin Tanner (57) ABSTRACT

A method includes deploying a bloused stent-graft into a main vessel such that a bloused section of the bloused stent-graft covers a branch vessel emanating from the main vessel. The bloused section includes loose graft cloth. A pressure differential between the main vessel and the branch vessel causes the bloused section to be forced into an ostium of the branch vessel creating a pocket aligned with the branch vessel. A distal tip of a puncture device is located in the pocket and thus aligned with the branch vessel. An outward force is applied to the puncture device to cause the distal tip of the puncture device to fenestrate the bloused section thus creating a collateral opening in the bloused section precisely aligned with the branch vessel.

8 Claims, 6 Drawing Sheets

BLOUSED STENT-GRAFT AND FENESTRATION METHOD

BACKGROUND OF THE INVENTION

1. Field of the Invention

The present invention relates to an intra-vascular device and method. More particularly, the present invention relates to a device for treatment of intra-vascular diseases.

2. Description of Related Art

A conventional main (vessel) stent-graft typically includes a radially expandable reinforcement structure, formed from a plurality of annular stent rings, and a cylindrically shaped layer of graft material, sometimes called graft cloth, defining a lumen to which the stent rings are coupled. Main stent-grafts are well known for use in tubular shaped human vessels.

To illustrate, endovascular aneurysmal exclusion is a method of using a main stent-graft to exclude pressurized fluid flow from the interior of an aneurysm, thereby reducing the risk of rupture of the aneurysm and the associated invasive surgical intervention.

Main stent-grafts with custom side openings are sometimes fabricated to accommodate the particular vessel geometry of each individual patient. Specifically, as the location of branch vessels emanating from a main vessel, e.g., having the aneurysm, varies from patient to patient, main stent-grafts are fabricated with side openings customized to match the position of the branch vessels of the particular patient. However, custom fabrication of main stent-grafts is relatively expensive and time consuming.

To avoid custom fabrication of main stent-grafts, side openings in the main stent-graft may be formed in situ. Illustratively, the main stent-graft is placed in the main vessel, e.g., the aorta, to exclude an aneurysm. Fenestrations may be made in situ to correspond to adjacent branches.

The graft material of the main stent-graft is pierced with a needle at the ostium of a branch vessel, e.g., the renal artery, emanating from the main vessel. Alignment of the needle with the center of the ostium of the branch vessel is accomplished using radiopaque markers on the needle. However, due to difficulties in accurately placement of the needle, the graft material of the main stent graft is often pierced offset from the center of the ostium of the branch vessel, which is undesirable.

SUMMARY OF THE INVENTION

In accordance with one example, a method includes deploying a bloused stent-graft into a main vessel such that a bloused section of the bloused stent-graft covers a branch vessel emanating from the main vessel. The bloused stent-graft includes a proximal section, a distal section, and the bloused section attached to and between the proximal section and the distal section. The bloused section includes loose graft cloth.

A pressure differential between the main vessel and the branch vessel causes the bloused section to be forced into an ostium of the branch vessel creating a pocket aligned with the branch vessel.

A distal tip of a puncture device is located in the pocket and thus aligned with the branch vessel. An outward force is applied to the puncture device to cause the distal tip of the puncture device to fenestrate the bloused section thus creating a collateral opening in the bloused section precisely aligned with the branch vessel.

As set forth above, by forming the bloused section with loose graft cloth, the pocket is self-aligned with the branch vessel as the loose graft cloth is forced into the branch vessel. The pocket, in turn, facilitates self-alignment of the puncture device with the branch vessel. Accordingly, fenestration of the bloused section with the puncture device creates the collateral opening precisely aligned with the branch vessel.

Embodiments are best understood by reference to the following detailed description when read in conjunction with the accompanying drawings.

BRIEF DESCRIPTION OF THE DRAWINGS

Common reference numerals are used throughout the drawings and detailed description to indicate like elements.

DETAILED DESCRIPTION

Figure 3:
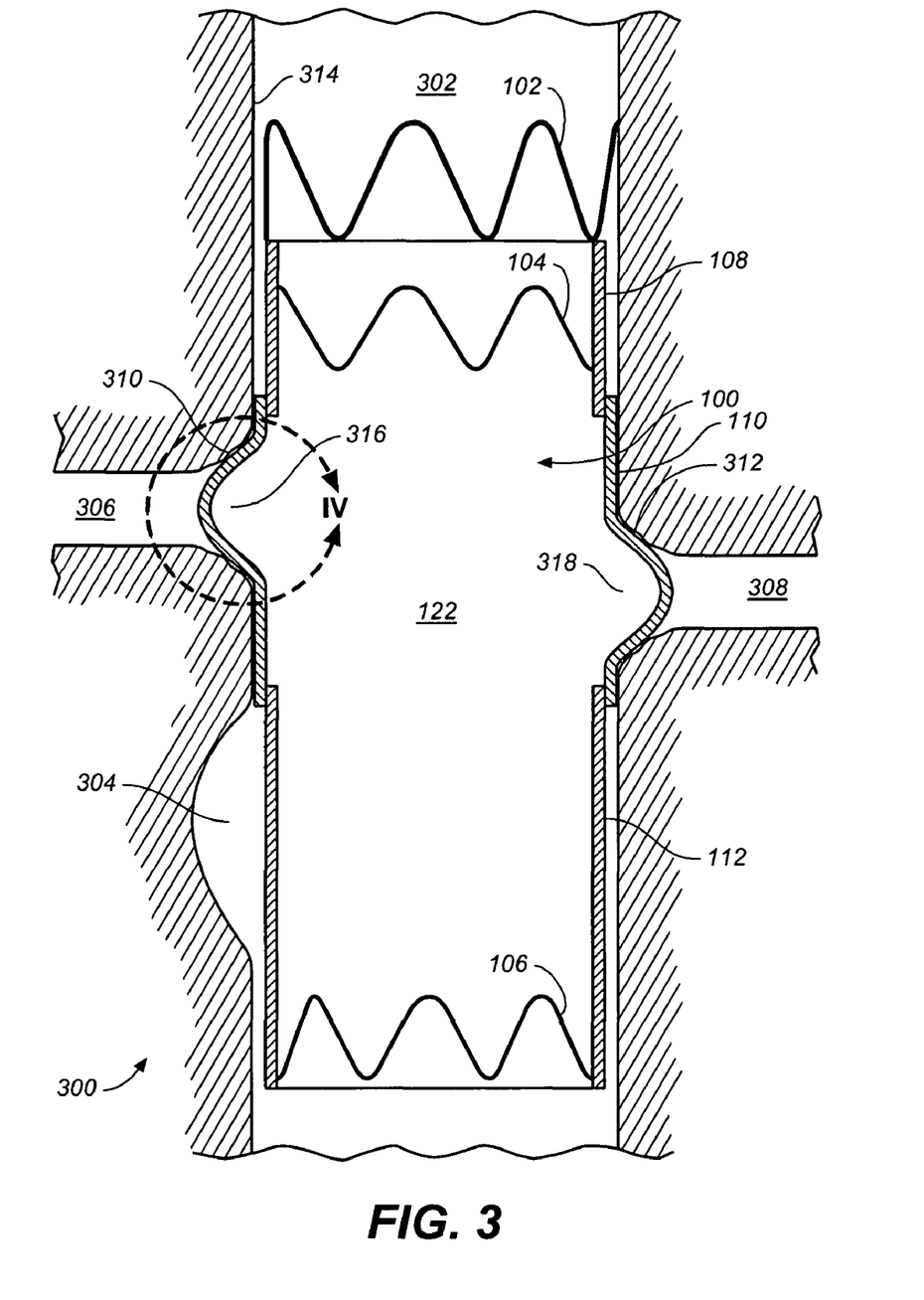
FIG. 3 is a cross-sectional view of a vessel assembly including the bloused stent-graft of FIGS. 1 and 2 in accordance with one embodiment.

Referring to FIG. 3, a method includes deploying a bloused stent-graft 100 into a main vessel 302 such that a bloused section 110 of bloused stent-graft 100 covers a branch vessel 306 emanating from main vessel 302. Bloused section 110 includes loose graft cloth.

Figure 4:
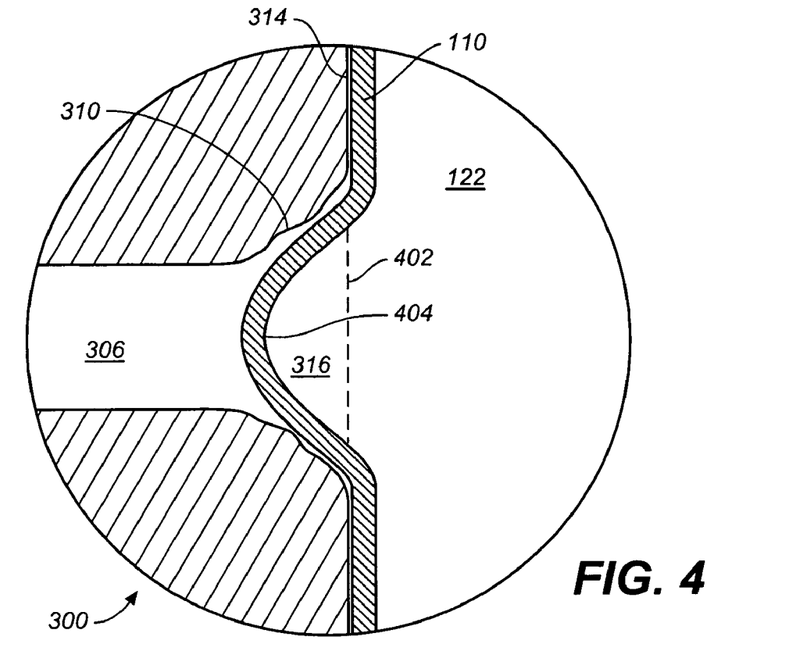
FIG. 4 is an enlarged cross-sectional view of a region IV of the vessel assembly of FIG. 3.

Referring now to FIGS. 3 and 4 together, a pressure differential between main vessel 302 and branch vessel 306 causes bloused section 110 to be forced into an ostium 310 of branch vessel 306 creating a pocket 316 precisely aligned with branch vessel 306.

Figure 5:
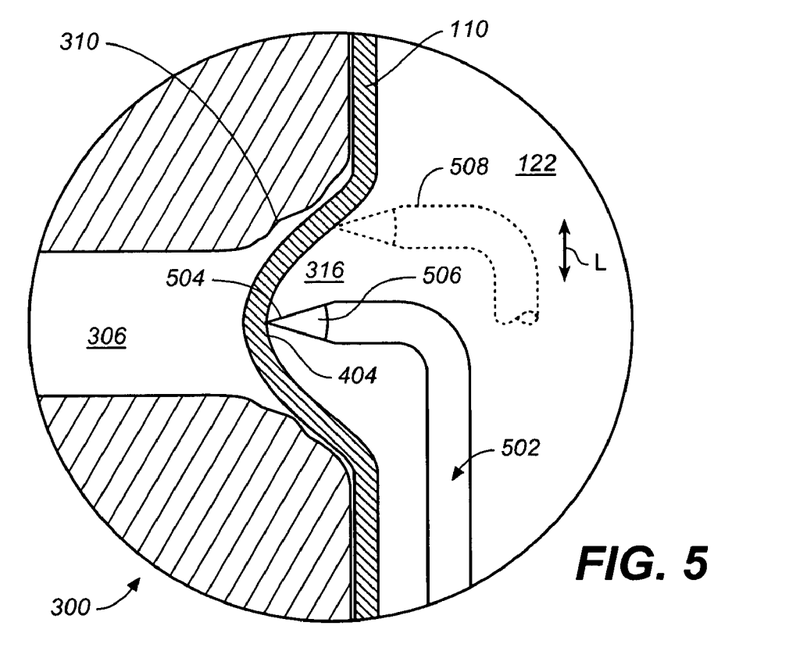
FIG. 5 is an enlarged cross-sectional view of the vessel assembly of FIG. 4 during fenestration of the bloused stent-graft.

Referring now to FIG. 5, a distal tip 504 of a steerable puncture device 502 is located in pocket 316 and thus precisely aligned with branch vessel 306. An outward force is applied to steerable puncture device 502 to cause distal tip 504 of steerable puncture device 502 to fenestrate bloused section 110 thus creating a collateral opening 602 (FIG. 6) in bloused section 110 precisely aligned with branch vessel 306.

Figure 5A:
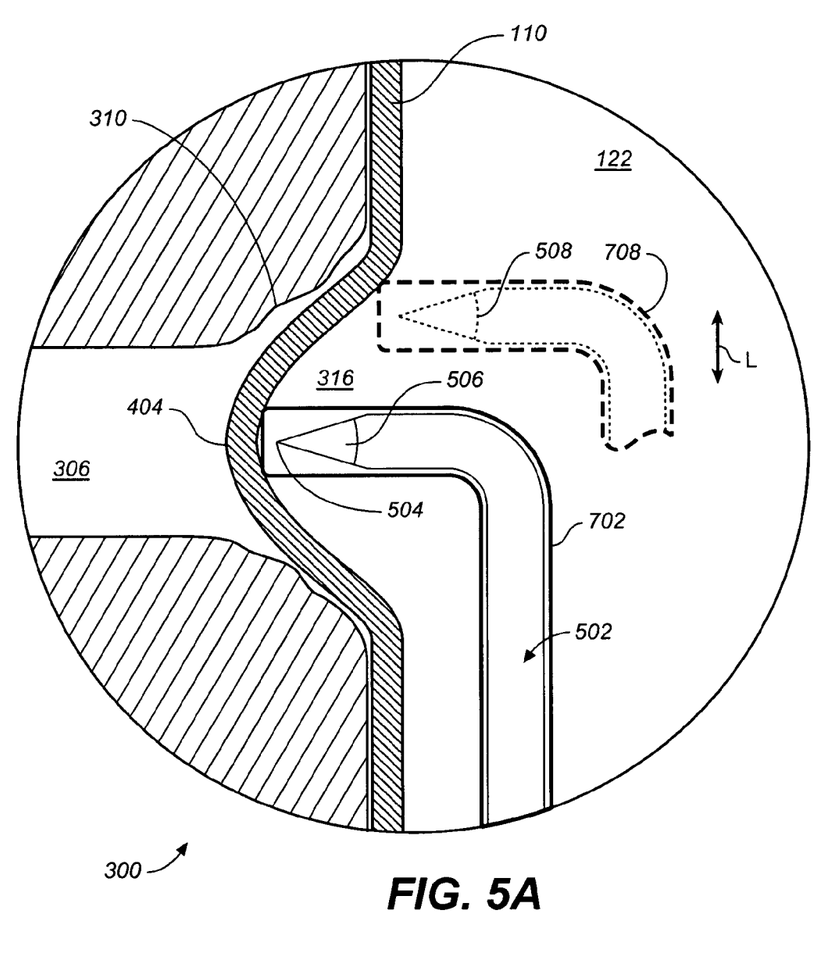
FIG. 5A is an enlarged schematic cross-sectional view of the vessel assembly of FIG. 4 showing an alternate configuration to that shown in FIG. 5.

Referring now to FIG. 5A, a distal tip 504 of a steerable puncture device 502 is contained within a guide catheter 702 located in pocket 316 and thus the puncture device is positioned to be precisely aligned with branch vessel 306. An outward force is applied to steerable puncture device 502 to move it forward within the guide catheter 702 to cause distal tip 504 of steerable puncture device 502 to fenestrate bloused section 110 thus creating a collateral opening 602 (FIG. 6) in bloused section 110 precisely aligned with branch vessel 306.

Figure 1:
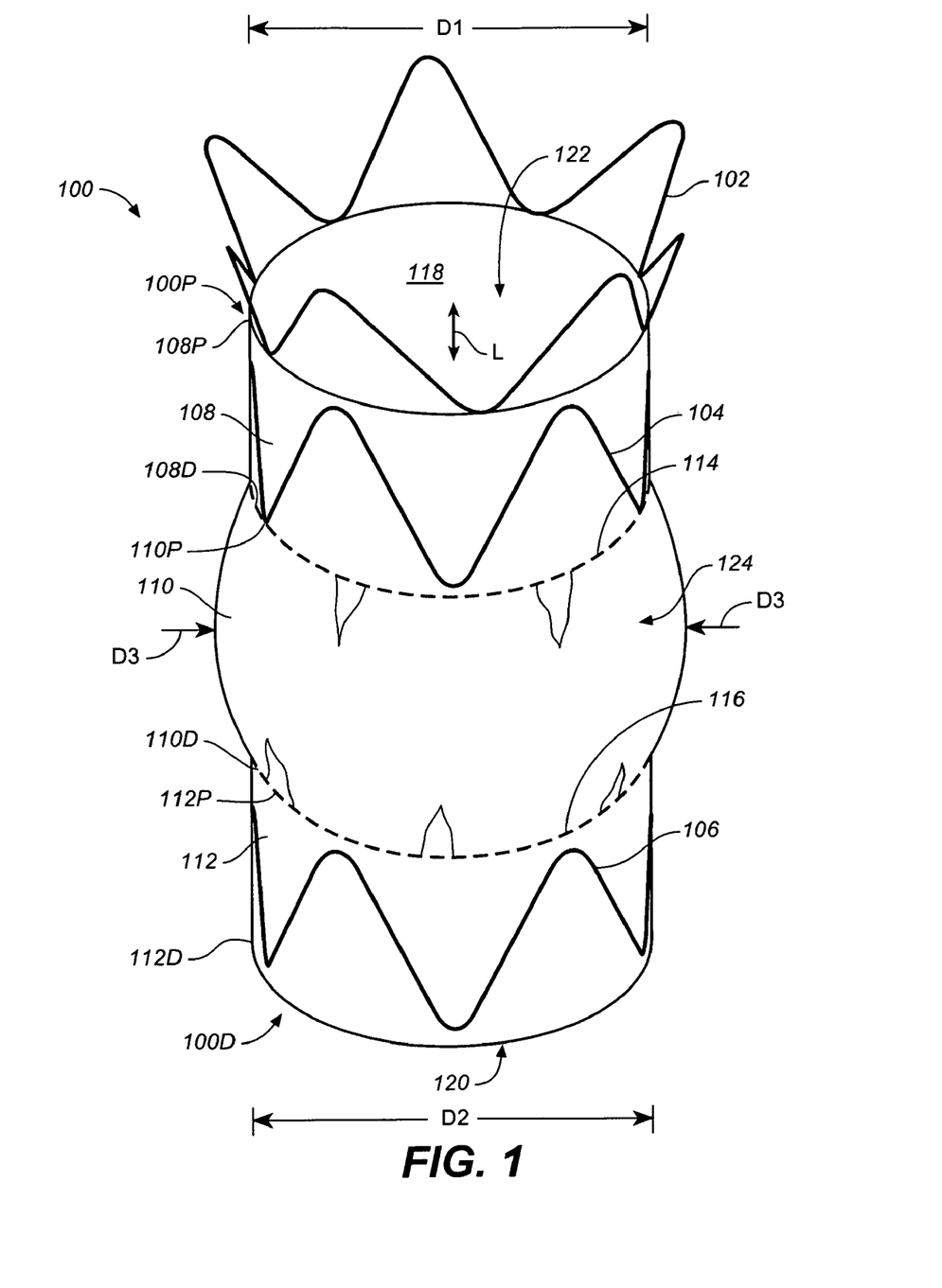
FIG. 1 is a perspective view of a bloused stent-graft in accordance with one embodiment.

More particularly, FIG. 1 is a perspective view of a bloused stent-graft 100, e.g., an abdominal aortic stent-graft, in accordance with one embodiment. Referring now to FIG. 1, bloused stent-graft 100 includes stent rings 102, 104, 106. Illustratively, stent rings 102, 104, 106 are self-expanding stent rings, e.g., formed of Nitinol. The inclusion of bare stent ring 102 is optional.

Figure 2:
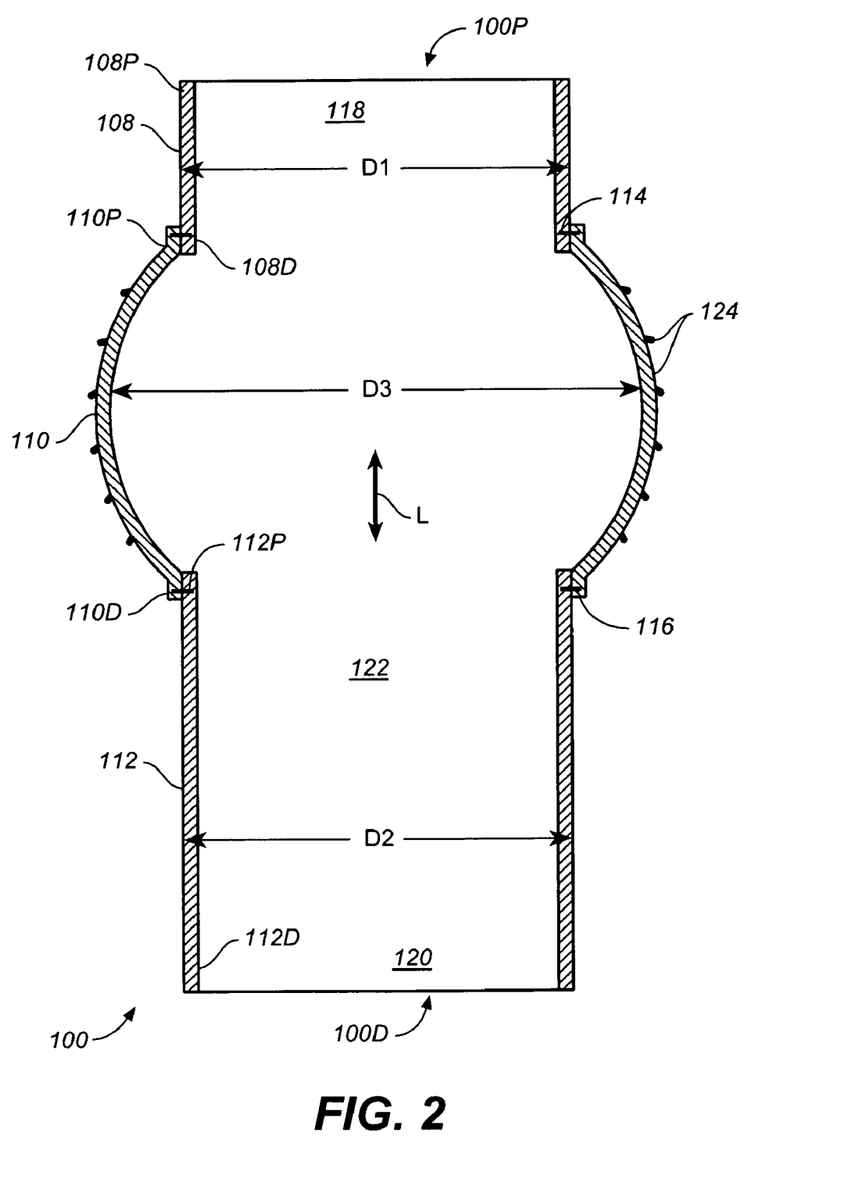
FIG. 2 is a cross-sectional view of the bloused stent-graft of FIG. 1.

FIG. 2 is a cross-sectional view of bloused stent-graft 100 of FIG. 1. In FIG. 2, stent rings 102, 104, 106 are not illustrated for clarity of presentation.

Referring now to FIGS. 1 and 2 together, bloused stent-graft 100 includes a proximal section 108, a bloused section 110, and a distal section 112, sometimes called a proximal segment, a bloused segment and a distal segment, respectively. Bloused section 110 is attached to and between proximal section 108 and distal section 112. A series of "V" shaped pleats are shown at the top and bottom of the bloused section, to cause the larger diameter cylindrical blouse section material to be narrowed to match the proximal 108 and distal section 112 smaller diameters.

As used herein, the proximal end of a prosthesis such as a stent-graft is the end closest to the heart via the path of blood flow whereas the distal end is the end furthest away from the heart during deployment. In contrast and of note, the distal end of the catheter is usually identified to the end that is farthest from the operator (handle) while the proximal end of the catheter is the end nearest the operator (handle).

For purposes of clarity of discussion, as used herein, the distal end of the catheter (steerable puncture device) is the end that is farthest from the operator (the end furthest from the handle) while the distal end of the prosthesis is the end nearest the operator (the end nearest the handle), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the stent-graft and delivery system description may be consistent or opposite in actual usage.

Proximal section 108 includes a proximal end 108P and a distal end 108D. Bloused section 110 includes a proximal end 110P and a distal end 110D. Distal end 108D of proximal section 108 is attached to proximal end 110P of bloused section 110 by an attachment means 114. Illustratively, attachment means 114 is stitching, adhesive, thermal bonding, or other attachment between proximal section 108 and bloused section 110.

Distal section 112 includes a proximal end 112P and a distal end 112D. Proximal end 112P of distal section 112 is attached to distal end 110D of bloused section 110 by an attachment means 116. Illustratively, attachment means 116 is stitching, adhesive, thermal bonding, or other attachment between bloused section 110 and distal section 112.

Bloused stent-graft 100 includes a proximal main opening 118 at a proximal end 100P on bloused stent-graft 100 and a distal main opening 120 at a distal end 100D of bloused stent-graft 100. Further, bloused stent-graft 100 includes a longitudinal axis L. A main lumen 122 is defined by bloused stent-graft 100 and extends generally parallel to longitudinal axis L and between proximal main opening 118 and distal main opening 120 of bloused stent-graft 100.

Proximal section 108 and distal section 112 are cylindrical having substantially uniform diameters D1, D2, respectively. In contrast, bloused section 110 has a non-uniform diameter having minimum diameters D1, D2 at proximal end 110P and distal end 110D and ballooning outward (increasing in diameter) therefrom.

In one embodiment, proximal section 108 is a first cylindrical piece of graft material, e.g., graft cloth, having a diameter D1. Distal section 112 is a second cylindrical piece of graft material, e.g., graft cloth, having a diameter D2. In the example illustrated in FIGS. 1 and 2, diameter D1 is equal to diameter D2, although in other examples diameter D1 is greater than diameter D2 or vice versa.

Bloused section 110 is formed from a third cylindrical piece of graft material, e.g., graft cloth, that has a diameter for example 50% larger than diameters D1, D2 of proximal section 108 and distal section 112, respectively. The ends of this cylindrical piece of graft material are attached, e.g., sewn, to proximal section 108 and distal section 112 creating bloused section 110. The bloused section must be large enough be seen under fluoroscopy which is expected when the peak diameter of the bloused section is from 10 to 60% larger than either adjacent section diameter D1 or D2. Accordingly, bloused section 110 balloons, sometimes called bulges, protrudes or extends, outward from proximal section 108 and distal section 112. The maximum diameter D3 of bloused section 110 is greater than diameter D1 or diameter D2. Bloused section 110 includes pleated loose graft cloth at each end where attachment to adjacent diameters D1, D2, sometimes called excess graft cloth, an overlarge bloused segment of graft cloth or slack graft cloth. In addition to pleating, another sewing method that could be used to attach the ends of the large diameter bloused section to the smaller diameter cylindrical section is "gathering" wherein what is meant here is that a tiny bit of extra cloth is gathered under each stitch to capture more material, i.e., a micropleat. Additionally the bloused portion could be specially woven to have cylindrically concave shape (so a cylindrical section of stent graft extends outwardly outside the proximal and distal diameters in an approximately spherical, ellipsoid, or similar continuous bulging surface shape) to avoid the need to have narrowed end portions such as provided by bunching, pleating, or gathering. The bloused section could also be constructed by using a cylindrical section of graft material of the larger bloused section maximum diameter and cutting pie shaped sections from both the proximal and distal end of the material at for example six evenly spaced circumferential locations around each end and sewing the sides of the remaining portions of the graft material (petal shaped sections) so that then the diameters of both the proximal and distal ends of the bloused section substantially match and can be sewn (or otherwise attached) to the proximal and distal substantially constant diameter end sections. In contrast, proximal section 108 and distal section 112 are circumferentially taut, i.e., have little to no give or slack.

Referring again to FIG. 1, in accordance with one example, bloused section 110 includes radiopaque ink 124 that allows visualization of bloused section 110. In one example, radiopaque ink 124 is applied, e.g., printed, as a stipple pattern to the graft material of bloused section 110. In this manner, flexibility of bloused section 110 is maintained while at the same time visualization of bloused section 110 is facilitated. However, in another embodiment, a bloused section similar to bloused section 110 is formed with an absence of radiopaque ink.

Stent ring 102, e.g., a first stent ring, is attached, e.g., sewn, to proximal section 108 at proximal end 108P thereof. Stent ring 102, sometimes called a suprarenal stent ring, extends proximally from proximal section 108. This stent ring is optional.

Stent ring 104, e.g., a second stent ring, is attached, e.g., sewn, to proximal section 108. Similarly, stent ring 106, e.g., a third stent ring, is attached, e.g., sewn, to distal section 112.

Stent rings 102, 104, 106, are self-expanding facilitating expansion, fixation, and sealing of bloused stent-graft 100 into the main vessel as discussed further below. In another example, a bloused stent-graft similar to bloused stent-graft 100 is formed with stent rings that are balloon expanded facilitating fixation and sealing of the bloused stent-graft into the main vessel. Bloused section 110 has an absence of stent rings.

Although three stent rings 102, 104, 106 are illustrated, in other examples, a bloused stent-graft similar to bloused stent-graft 100 is formed with more or less than three stent rings or other self-expanding members.

FIG. 3 is a cross-sectional view of a vessel assembly 300 including bloused stent-graft 100 of FIGS. 1 and 2 in accordance with one embodiment. Referring now to FIG. 3, a main vessel 302, e.g., the aorta, includes an aneurysm 304. Bloused stent-graft 100, sometimes called a prosthesis, is deployed into main vessel 302 to exclude aneurysm 304 using any one of a number of techniques well known to those of skill in the art.

Emanating from main vessel 302 is a first branch vessel 306 and a second branch vessel 308, sometimes called visceral branches of the abdominal aorta. The location of branch vessels 306, 308 vary from patient to patient. Examples of branch vessels include the renal arteries (RA) and the superior mesenteric artery (SMA).

Bloused stent-graft 100 is deployed such that bloused section 110 is aligned with branch vessels 306, 308. Stated another way, bloused stent-graft 100 is deployed such that blouse section 110 covers ostia (plural of ostium) 310, 312 of branch vessels 306, 308, respectively.

Proximal section 108 is located proximally to ostia 310, 312 of branch vessels 306, 308. Accordingly, bloused stent-graft 100 is deployed with fixation and sealing superior to branch vessels 306, 308. Distal section 112 is located distally to ostia 310, 312 of branch vessels 306, 308.

Stent rings 102, 104, 106 are radially expandable reinforcement structures that self-expand into a vessel wall 314 of main vessel 302 thus anchoring bloused stent-graft 100 in place. Bloused stent-graft 100 is delivered to main vessel 302 and deployed therein using any one of a number of techniques well known to those of skill in the art.

Once anchored within main vessel 302, blood flows through main lumen 122 and more generally through bloused stent-graft 100 thus excluding aneurysm 304. Further, blood pressure within bloused stent-graft 100 creates pockets 316, 318 within bloused section 110. More particularly, the pressure inside of bloused stent-graft 100 is greater than the pressure within branch vessels 306, 308. Due to this pressure differential, bloused section 110, which is loose, is forced into ostia 310, 312 of branch vessels 306, 308 creating pockets 316, 318, respectively. Accordingly, pockets 316, 318, sometimes called first and second pockets, are precisely aligned with ostia 310, 312, sometimes called first and second ostia, of branch vessels 306, 308, sometimes called first and second branch vessels, respectively.

To illustrate, FIG. 4 is an enlarged cross-sectional view of a region IV of vessel assembly 300 of FIG. 3. As illustrated in FIG. 4, bloused section 110 follows the contour of vessel wall 314 of main vessel 302. Further, bloused section 110 follows the contour of ostium 310, which is illustrated as being enlarged due to disease.

Pocket 316 is a region defined by the portion of bloused section 110 extending radially outward into branch vessel 306. Pocket 316 is the region between an imaginary cylindrical surface defined by vessel wall 314 as indicated by the dashed line 402 in FIG. 4 to the portion of bloused section 110 extending radially outward into branch vessel 306. Pocket 316 includes an apex 404, i.e., the most radial outward portion of bloused section 110. Bloused section 110 tapers radially outward in a rounded conical shape to apex 404 from vessel wall 314. Apex 404, and more generally, pocket 316, is precisely aligned with branch vessel 306.

Returning to FIG. 3, the location of branch vessels 306, 308 are longitudinally offset from one another. However, as bloused section 110 is aligned with both of branch vessels 306, 308, pocket 318 is precisely aligned with branch vessel 308 in a manner similar to that discussed above regarding alignment of pocket 316 with branch vessel 306 and so is not repeated here.

FIG. 5 is an enlarged cross-sectional view of vessel assembly 300 of FIG. 4 during fenestration of bloused stent-graft 100. Referring now to FIG. 5, to form a side opening, sometimes called a collateral opening, in bloused stent-graft 100, and more particularly, bloused section 110, corresponding to (at) branch vessel 306, a steerable puncture device 502 is advanced to the location of branch vessel 306. Steerable puncture devices similar to steerable puncture device 502 are well known to those of skill in the art.

Steerable puncture device 502 is oriented radially, e.g., at a 90 degree angle, relative to longitudinal axis L and thus points at bloused section 110 of bloused stent-graft 100. More particularly, a distal tip 504 of steerable puncture device 502 is located within pocket 316 and rests against (contacts) apex 404. Accordingly, steerable puncture device 502 is precisely aligned with branch vessel 306.

In one example, steerable puncture device 502 includes a radiopaque marker 506 that allows visualization of steerable puncture device 502. As set forth above, in one example, bloused section 110 includes radiopaque ink 124 that allows visualization of bloused section 110. Accordingly, both steerable puncture device 502 and bloused section 110 are visualized to ensure precise alignment of steerable puncture device 502 within pocket 316.

Further, in one example, in the event of initial misalignment of steerable puncture device 502 with apex 404 as illustrated by the phantom lines 508, outward radial force on steerable puncture device 502 causes steerable puncture device 502 to slide down the taper of pocket 316 and to apex 404. Once located at apex 404, further outward force on steerable puncture device 502 causes distal tip 504, e.g., a sharp tip, to fenestrate (penetrate) bloused section 110 precisely in alignment with branch vessel 306.

FIG. 5A is an enlarged cross-sectional view of vessel assembly 300 of FIG. 4 during an alternate method of fenestration of bloused stent-graft 100. Referring now to FIG. 5A, to form a side opening, sometimes called a collateral opening, in bloused stent-graft 100, and more particularly, bloused section 110, corresponding to (at) branch vessel 306, a steerable guide catheter 702 (such as those manufactured by Enpath and Cardima) having a puncture device 502 contained therein is advanced to the location of branch vessel 306. The end of the steerable guide catheter is blunt to minimize the chances of the end of the device catching in the graft cloth. A blunt or rounded end permits smooth sliding of the end of steerable catheter in contact with the graft (pocket) surface. The puncture device can be advanced simultaneously with the steerable guide catheter, or can be inserted within the steerable guide catheter after the steerable guide catheter has been positioned within the bloused pocket.

The end of steerable guide catheter 702 with the puncture device 502 contained therein is oriented radially, e.g., at a 90 degree angle, relative to longitudinal axis L and thus points at bloused section 110 of bloused stent-graft 100. More particularly, a distal tip of the guide catheter 702 is located within pocket 316 and rests against (contacts) apex 404. Accordingly, the puncture device 502 contained in the steerable guide catheter 702 is precisely aligned with branch vessel 306.

As is well known in the art, steerable guide catheters are constructed of materials which provide visualization of its position under fluoroscopy. As set forth above, in one example, bloused section 110 includes radiopaque ink 124 that allows visualization of bloused section 110. Accordingly, both steerable guide catheter 702 and bloused section 110 are visualized to ensure precise alignment of the steerable guide catheter 702 and puncture device 502 within pocket 316.

Further, in one example, in the event of initial misalignment of the steerable guide catheter 702 with the puncture device 502 contained therein with apex 404 as illustrated by the phantom lines 708, outward radial force on the guide catheter 702 causes the blunt end of the guide catheter 702 to slide down the taper of pocket 316 and to apex 404. Once the steerable guide catheter is located at apex 404, the puncture device is advanced within the steerable guide catheter 702 to contact the bloused section of graft material, further outward force on the puncture device 502 allows its distal tip 504, e.g., a sharp tip, to fenestrate (penetrate) bloused section 110 precisely in alignment with branch vessel 306.

Figure 6:
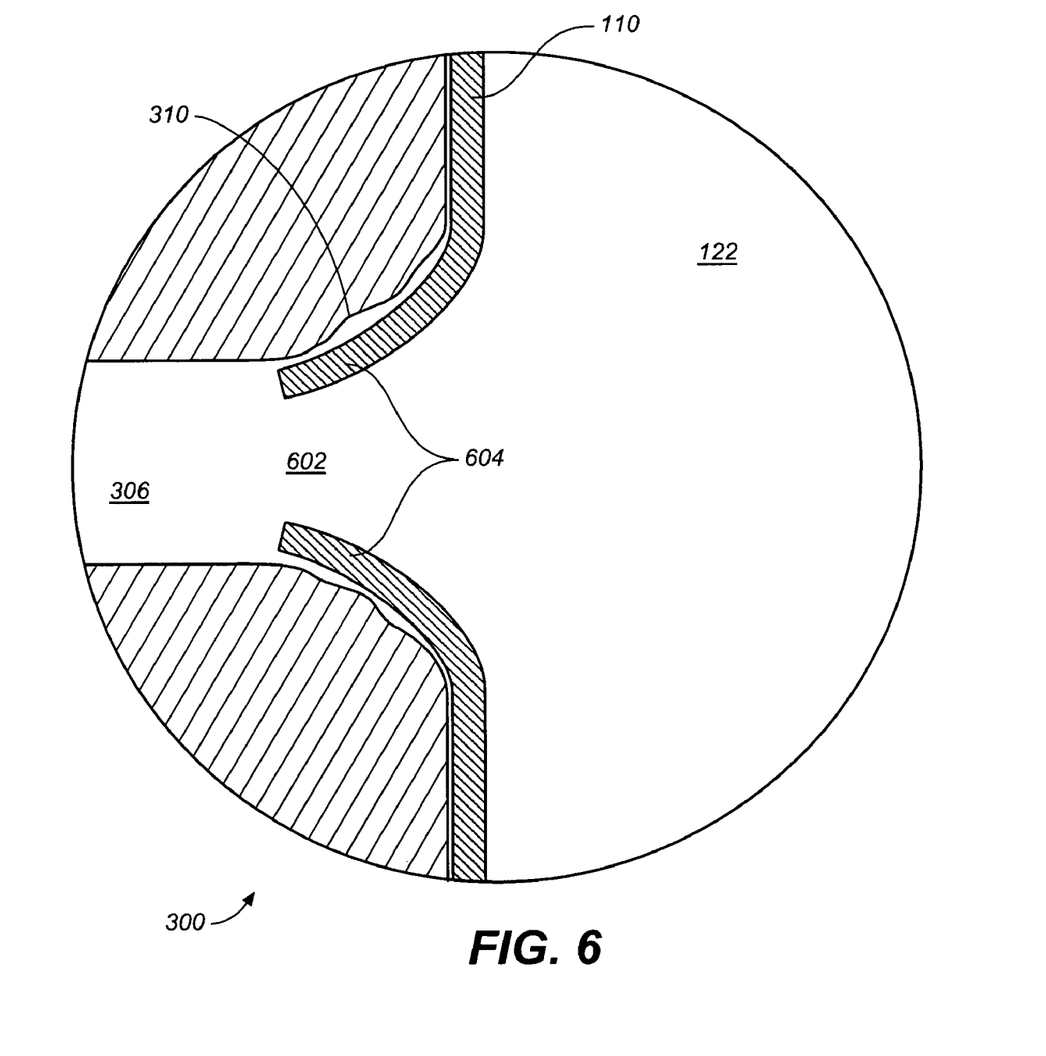
FIG. 6 is an enlarged schematic cross-sectional view of the vessel assembly of FIG. 5 after fenestration of the bloused stent-graft.

FIG. 6 is an enlarged schematic cross-sectional view of vessel assembly 300 of FIGS. 5 and 5A after fenestration of bloused stent-graft 100. Referring now to FIGS. 5, 5A, and 6 together, after fenestration of bloused section 110 with steerable puncture device 502 and removal of steerable puncture device 502, a collateral opening 602 is formed in bloused stent-graft 100. More particularly, collateral opening 602 is formed in bloused section 110. Collateral opening 602 facilitates blood flow from main lumen 122 of bloused stent-graft 100 through collateral opening 602 and into branch vessel 306, thus perfusing branch vessel 306. Further, bloused section 110 follows the contour of ostium 310 effectively forming a branch graft 604 extending into branch vessel 306.

By forming bloused section 110 with loose graft cloth, pocket 316 is self-aligned with branch vessel 306 as the loose graft cloth is forced into branch vessel 306. Pocket 316, in turn, facilitates self-alignment of steerable puncture device 502 with branch vessel 306. Accordingly, fenestration of bloused section 110 with steerable puncture device 502 creates collateral opening 602 precisely aligned with branch vessel 306.

Returning now to FIGS. 3, 4, 5, 5A, and 6 together, steerable puncture device 502 is used to form a collateral opening in bloused stent-graft 100 in alignment with branch vessel 308 in a similar manner to formation of collateral opening 602 as discussed above and so is not repeated here. In accordance with the above example, a method of fenestration in situ of bloused stent-graft 100 is provided to address the problem of perfusing visceral branches of the abdominal aorta with an abdominal aortic aneurysm 304 in which bloused stent-graft 100 is deployed with fixation and sealing superior to the renal arteries (RA) and superior mesenteric artery (SMA).

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A bloused stent-graft comprising:
   a proximal section comprising a first cylindrical piece of graft material having a first diameter;
   a first stent ring attached to said proximal section;
   a distal section comprising a second cylindrical piece of graft material having a second diameter;
   a second stent ring attached to said distal section; and
   a bloused section attached to and between said proximal section and said distal section, said bloused section comprising loose graft cloth, said bloused section extending outward from said proximal section and said distal section, wherein said bloused section comprises a third cylindrical piece of graft material having a third diameter greater than said first diameter and said second diameter, said bloused section comprising v-shaped pleats to cause said third diameter to be narrowed to said first diameter and said second diameter at ends of said third cylindrical piece of graft material, wherein said ends of said third cylindrical piece of graft material are attached to said proximal section and said distal section to form said bloused section,
   wherein said proximal section comprises a proximal end and a distal end, said distal end being attached to a proximal end of said bloused section by stitching a first set of, said v-shaped pleats having open ends at said proximal end of said bloused section and extending from said open ends to terminate at points of said first set of v-shaped pleats, said points of said first set of said v-shaped pleats terminating at an unpleated section of said bloused section, said points extending in the direction of said distal section, and
   wherein a distal end of said bloused section is attached to a proximal end of said distal section by stitching a second set of, said v-shaped pleats having open ends at said distal end of said bloused section and extending from said open ends at said distal end to terminate at points of said second set of said v-shaped pleats, said points of said second set of said v-shaped pleats terminating at said unpleated section of said bloused section, said points of said second set of said v-shaped pleats extending in the direction of the proximal section.

2. The bloused stent-graft of claim 1 wherein said bloused stent-graft defines a main lumen extending generally parallel to a longitudinal axis of said bloused stent-graft and between a proximal main opening and a distal main opening of said bloused stent graft.

3. The bloused stent-graft of claim 1 wherein said bloused section has a non-uniform diameter.

4. The bloused stent-graft of claim 3 wherein said bloused section has said first diameter at said proximal end of said bloused section and has said second diameter at said distal end of said bloused section, said bloused section increasing in diameter from said proximal end and said distal end.

5. The bloused stent-graft of claim 4 wherein said bloused section balloons outward from said proximal section and said distal section.

6. The bloused stent-graft of claim 4 wherein said loose graft cloth is slack and said proximal section and said distal section are taut.

7. The bloused stent-graft of claim 1 wherein said bloused section comprises radiopaque ink.

8. The bloused stent-graft of claim 1 further comprising a collateral opening in said bloused section.

* * * * *